(12) United States Patent
Bailon et al.

(10) Patent No.: US 7,201,897 B2
(45) Date of Patent: Apr. 10, 2007

(54) INTERFERON CONJUGATES

(75) Inventors: Pascal Sebastian Bailon, Florham Park, NJ (US); Alicia Vallejo Palleroni, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 384 days.

(21) Appl. No.: 10/377,892

(22) Filed: Feb. 27, 2003

(65) Prior Publication Data

US 2004/0030101 A1 Feb. 12, 2004

Related U.S. Application Data

(63) Continuation of application No. 09/255,948, filed on Feb. 23, 1999, now abandoned, which is a continuation of application No. 08/842,462, filed on Apr. 24, 1997, now abandoned.

(60) Provisional application No. 60/039,535, filed on Mar. 6, 1997, provisional application No. 60/018,834, filed on May 31, 1996.

(51) Int. Cl.
*A61K 38/21* (2006.01)
*C07K 1/113* (2006.01)
*C07K 14/56* (2006.01)

(52) U.S. Cl. .............. 424/85.7; 530/351; 530/409

(58) Field of Classification Search ........ 530/351, 530/405, 409; 424/85.1, 85.4, 85.7
See application file for complete search history.

(56) References Cited

U.S. PATENT DOCUMENTS

| 4,609,546 A | 9/1986 | Hiratani ............... 514/2 |
| 4,681,848 A | 7/1987 | Tsukamoto et al. ..... 435/240 |
| 4,766,106 A | 8/1988 | Katre et al. ............. 514/12 |
| 4,911,888 A | 3/1990 | Fikentscher et al. ....... 422/16 |
| 4,935,465 A | 6/1990 | Garman ................. 525/54.1 |

(Continued)

FOREIGN PATENT DOCUMENTS

EP 0 400 472 12/1990

(Continued)

OTHER PUBLICATIONS

Morpurgo, et al., "Covalent Modification of Mushroom Tyrosinase with Different Amphiphic Polymers for Pharmaceutical and Biocatalysis Applications", *Applied Biochemistry and Biotechnology*, (1996), 56(1): 59-72.

(Continued)

*Primary Examiner*—Jeffrey Edwin Russel
(74) *Attorney, Agent, or Firm*—George W. Johnston; Dennis P. Tramaloni (57) ABSTRACT

Physiologically active PEG-IFNα conjugate having a formula as follows:

$$\text{ROCH}_2\text{CH}_2(\text{OCH}_2\text{CH}_2)_n-\text{O}-\overset{\text{O}}{\underset{\|}{\text{C}}}-\text{NH}$$
$$|$$
$$(\text{CH}_2)_4$$
$$|$$
$$\text{R'OCH}_2\text{CH}_2(\text{OCH}_2\text{CH}_2)_{n'}-\text{O}-\overset{\text{O}}{\underset{\|}{\text{C}}}-\text{NH}-\overset{\text{CH}}{\underset{\|}{\text{C}}}-\text{X}-\text{IFN}\alpha$$

I

18 Claims, 6 Drawing Sheets

U.S. PATENT DOCUMENTS

| | | | | |
|---|---|---|---|---|
| 5,122,614 | A | | 6/1992 | Zalipsky ..................... 548/520 |
| 5,145,773 | A | * | 9/1992 | Albino et al. .............. 435/7.23 |
| 5,281,698 | A | | 1/1994 | Nitecki ....................... 530/351 |
| 5,359,030 | A | | 10/1994 | Ekwuribe et al. ........... 530/303 |
| 5,382,567 | A | | 1/1995 | Karasiewicz et al. ....... 530/351 |
| 5,438,040 | A | | 8/1995 | Ekwuribe ....................... 514/3 |
| 5,595,732 | A | | 1/1997 | Hakini et al. .............. 424/85.7 |
| 5,643,575 | A | | 7/1997 | Martinez et al. .......... 424/194.1 |
| 5,762,923 | A | | 6/1998 | Gross et al. ............... 424/85.7 |
| 5,932,462 | A | | 8/1999 | Harris et al. ................. 435/188 |
| 6,113,906 | A | | 9/2000 | Greenwald et al. ....... 424/194.1 |
| 2004/0185489 | A1 | * | 9/2004 | Certa et al. ..................... 435/6 |

FOREIGN PATENT DOCUMENTS

| | | |
|---|---|---|
| EP | 510 356 | 10/1992 |
| EP | 0 576 192 | 12/1993 |
| EP | 0 103 898 | 3/1994 |
| EP | 0 593 868 | 4/1994 |
| EP | 0 736 303 | 10/1996 |
| WO | WO 84/04745 | 12/1984 |
| WO | WO 87/00056 | 1/1987 |
| WO | WO 92/21691 | 12/1992 |
| WO | WO 95/11924 | 5/1995 |
| WO | WO 95/13090 | 5/1995 |
| WO | WO 95/21629 | 8/1995 |
| WO | WO 96/11953 | 4/1996 |
| WO | WO 96/21469 | 7/1996 |
| WO | WO 97/18832 | 5/1997 |

OTHER PUBLICATIONS

C.S. Monfardini, et al., A Branched Monomethoxypoly(ethylene glycol) for protein modification, *Bioconjugate Chem.* (1995) 6:62-69.

S. Pestka, The Human Interferons-From Protein Purification and Sequence to Cloning and Expression in Bacteria: Before, Between, and Beyond. *Arch. Biochem. Biophys.* (1983) 221(1): 1-37.

S. Pestka, "The Purification and Manufacture of Human Interferons" *Sci. Am.*(1983) 249(2):36-43.

S. Rubenstein, et al., "Convenient Assay for Interferons," *J. Virol.* (1981) 37:755-758.

Y. Inada, et al., "Polyethylene Glycol(PEG)-Protein Conjugates: Application to Biomedical and Biotechnological Processes, J. Bioact. and Compatible Polymers," *J. Bioact. and Compatible Polymers*,(1990) 5:343-364.

C. Delgado, et al., "The Uses and Properties of PEG-Linked Proteins," *Critical Reviews in Therapeutic Drug Carrier Sysytems*,(1992) 9(3,4):249-304.

N.V. Katre, et al., "The Conjugation of Proteins with PEG and Other Polymers; Altering Properties to Enhance Their Therapeutic Potential," *Advance Drug Delivery Reviews*,(1993) 10:91-114.

N.V. Katre, et al,. "Chemical Modifications of Interleukin-2 by Polyethyleneglycol Increases Its Potency in the Murine Meth A Sarcoma Model," *Proc. Natl. Acad. Sci. USA*,(1987) 84:1487-1491.

R.Satake-Ishikawa, et al., "Chemical Modification of Recombinant Human Granulocyte Colony Stimulating Factor by Polyethyleneglycol Increases Its Biological Activity In Vivo," *Cell Structure and Function*,(1992) 17:157-160.

Y. Tsutsumi, et al., "Chemical Modification of Natural Tumor Necrosis Factor-α With Polyethylene Glycol Increases Its Potency, ," *JpnJ. Cancer Res.*,(1994) 85:9-12.

H. Inoue, et al., "A Highly Enhanced Thrombopoietic Activity By Polyethylene Glycol-Modified Recombinant IL-6, J. Lab. Clin. Med.," *J. Lab. Clin. Med.*,(1994) 124:529-536.

S.M. Chamow, et al., "Modification of CD4 Immunoadhesion with Monomethoxypoly (Ethylene Glycol) Aldehyde Via Reductive Alkylation," *Bioconj. Chem..*,(1994) 5:133-140.

E.C. Borden, et al., Comparative Antiproliferative Activity In Vitro of Natural Interferons α and β for Diploid and Transformed Human Cells, *Can. Res.*(1982) 42: 4948-4953.

Yoshinaga, et al., *J. Bioact. Compatible Polym.* (1987) 4:17-24.

Yoshinaga, et al., *J. Bioact. Compatible Polym.* (1987) 2:49-56.

Matsushima, A., et al., *Chem Letter Pages* (1980) pp. 773-776.

Yamasaki, et al., *Agric Biol. Chem.* (1990) 54:2635-2640.

Yamasaki, et al., *Agric Biol. Chem.* (1988) 52:2125-2127.

Truitt, et al., "Pharmacodynamic and Preliminary Pharmacokinetic Evaluation of Pegylated Derivatives of Interferon-Alpha 2A," *Proc. Annu. Meet AM Assoc. Canc. Res.*, (1994) vol. 35, A2370.

Palleroni, et al., "The in Vivo Fate of PEG-Interferon Alphah 2a (ro 25-3036) in Tumor Bearing Mice (Meeting Abstract)," *Proc. Annu. Meet AM Assoc Canc. Res.* (1994) vol. 35, A1845.

Monkarsh, et al., "Positional Isomers of Monopegylated Interferon α-2a: Isolation, Characterization, and Biological Activity, *Analytical Biochemistry* (1997), vol. 247, pp. 434-440.

Lam, et al., "Dose-Dependent Acute Clearance of Hepatitis C Genotype 1 Virus With Interferon Alpha," *Hepatology.* (1997) 26(1):226-231.

Fung, et al., "Strategies For The Preparation and Characterization of Polyethylene Glycol (PEG) Conjugated Pharmaceutical Proteins," *Polym. Prep.* (1997) 38: 565-566.

* cited by examiner

INTERFERON CONJUGATES

This is a continuation of application Ser. No. 09/255,948, filed Feb. 23, 1999, abandoned, which is a continuation of application Ser. No. 08/842,462, filed Apr. 24, 1997, abandoned, which claims the benefit of priority under 35 U.S.C. § 119(e) of provisional applications No. 60/018,834, filed May 31, 1996, and 60/039,535, filed Mar. 6, 1997, the contents of which are incorporated herein by reference.

BACKGROUND OF THE INVENTION

Interferon, in particular interferon α-2a, is a pharmaceutically active protein which has antiviral and antiproliferative activity. For example interferon is used to treat hairy cell leukemia and Kaposi's sarcoma, and is active against hepatitis. In order to improve stability and solubility, and reduce immunogenicity, pharmaceutically active proteins such as interferon may be conjugated to the polymer polyethylene glycol (PEG).

The bioavailability of protein therapeutics are often limited due to their short plasma half-life, thus preventing them from attaining their maximum clinical potency. In recent years, PEG conjugated biomolecules have been shown to possess clinically useful properties (Inada, Delgado, Katre I). Among these are better physical and thermal stability, protection against susceptibility to enzymatic degradation, increased solubility, longer in vivo circulating half-life and decreased clearance, enhancing potency. It has been reported that branched PEG conjugates exhibit increased pH and thermal stability and greater stability towards proteolytic digestion than linear PEG conjugates. (Monfardini). Other properties of PEG proteins are reduced immunogenicity and antigenicity, as well as reduced toxicity. Another effect of PEGylation of certain proteins may be reduced in vitro activity accompanied by enhanced in vivo activity. This has been observed in G-CSF (Satake-Ishikawa), IL-2 (Katre II), TNF-α (Tsutsumi), IL-6 (Inoue) CD4-IgG (Chamow), among others.

SUMMARY OF THE INVENTION

Applicants have now observed that in the case of interferon, PEGylation reduces in vitro antiviral activity but increases antiproliferative activity in human tumor cells. However the new PEG interferon conjugate of this invention has surprising properties in that the in vivo antiproliferative activity of the PEG interferon is much higher than that not only of interferon but of other PEG interferon conjugates. Although the in vivo antiproliferative activity of the conjugate is much increased over other PEG interferon-α conjugates, the reduction in antiviral activity is similar. In addition, the PEG interferon-α conjugate of this invention is non-immunogenic, it elicits virtually no antibody formation. In contrast, other PEG interferon-α conjugates do elicit limited antibody formation.

Accordingly, the invention is a new class of PEG derivatives of interferonα (IFNα). The conjugate of this invention has a branched PEG structure, as can be seen below. The branched PEG has the advantage of allowing the attachment of 2 linear PEG molecules at a single site, thus doubling the attached PEG mass without multiple sites of PEGylation.

Compared to unmodified IFNα (i.e. IFNα without a PEG attached), the conjugate has an increased circulating half-life and plasma residence time, reduced immunogenicity, decreased clearance, and increased in vivo antiproliferative activity, concomitant with decreased in vitro antiviral activity. Compared with other PEG-IFNα conjugates, the conjugate of this invention has a much greater in vivo antiproliferative activity, disproportionate to the enhancement or reduction that occurs in its other characteristics, and virtually no immunogenicity.

The physiologically active PEG-IFNα conjugate species of this invention has the formula:

I

The conjugate of this invention has the same uses as IFNα, for example, antiproliferative uses. In particular, the PEG interferon-α conjugates of this invention are useful to treat such diseases as hairy cell leukemia, CML, and Kaposi's sarcoma, in the same way IFNα (especially IFNα2a), are used to treat these diseases. However, the conjugate of this invention has improved properties including superior stability, greater solubility, enhanced circulating half-life and plasma residence times. In addition, these conjugates have in vivo antiproliferative activity that is superior to IFNα.

DESCRIPTION OF THE DRAWINGS

All animals received a subcutaneous implant of $2 \times 10^6$ human renal A498 cells on Study Day-33. On Study Day 0 PEG-IFN alpha-2A treatment was initiated. The indicated amount (30, 60, 120 or 300 µg) of PEG2-IFN alpha-2a was administered subcutaneously under the opposite flank of the tumor, 1 time per week for a four week period.

All animals received a subcutaneous implant of $2 \times 10^6$ human renal A498 cells on Study Day-33. On Study Day 0 IFN alpha-2a treatment was initiated. The indicated amount (10, 20, 40 or 100 µg) of IFN alpha-2a was administered subcutaneously under the opposite flank of the tumor, 3 times per week for a four week period.

All animals received a subcutaneous implant of $2 \times 10^6$ human renal ACHN cells on Study Day-25. On Study Day 0 PEG2-IFN alpha-2a treatment was initiated. The indicated amount (30, 60, 120 or 300 µg) of PEG2-IFN alpha-2a was administered subcutaneously under the opposite flank of the tumor, 1 time per week for a five week period.

All animals received a subcutaneous implant of $2 \times 10^6$ human renal ACHN cells on Study Day-25. On Study Day 0 IFN alpha-2a treatment was initiated. The indicated amount (10, 20, 40 or 100 µg) of IFN alpha-2a was admin

All animals received a subcutaneous implant of 2×10⁶ human renal G402 cells on Study Day-45. On Study Day 0 PEG2-IFN alpha-2a treatment was initiated. The indicated amount (30, 60, 120 or 300 μg) of PEG2-IFN alpha-2a was administered subcutaneously under the opposite flank of the tumor, 1 time per week for a five week period.

All animals received a subcutaneous implant of 2×10⁶ human renal G402 cells on Study Day-45. On Study Day 0 IFN alpha-2a treatment was initiated. The indicated amount of (10, 20, 40 or 100 μg) of IFN alpha-2a was administered subcutaneously under the opposite flank of the tumor, 3 times per week for a five week period.

DETAILED DESCRIPTION OF THE INVENTION

The claimed invention is a physiologically active PEG-IFNα conjugate having the formula

I where R and R' are independently lower alkyl; X is NH or O (X is at least one of the functional groups in the IFNα molecule selected from NH₂ or OH); n and n' are integers having a sum of from 600 to 1500; and the average molecular weight of the polyethylene glycol units in said conjugate is from about 26,000 daltons to about 66,000 daltons. The conjugate of formula I has a branched structure, in that two PEG moieties are attached to the protein via a single linkage.

The numbers n and n' are selected such that the resulting conjugate of Formula I has a physiological activity of IFNα, which activity may represent the same as, more than, or a fraction of the corresponding activity of unmodified IFNα. n and n' (n and n' may be the same or different) represent the number of ethylene glycol units in the PEG. A single PEG unit of OCH₂CH₂ has a molecular weight of about 44 daltons. The molecular weight of the conjugate (excluding the molecular weight of the IFNα) depends on the numbers n and n'. The sum of n and n' for the conjugate of Formula I is from 600 to 1500, producing a conjugate having a total average molecular weight of PEG units of from about 26,000 to 66,000 and preferably from about 35,000 to 45,000 daltons, and especially about 39,000 to 45,000 daltons, with 40,000 daltons especially preferred. A preferred sum of n and n' is from about 800 to 1200, with the average sum being from about 850 to 1000, and a preferred sum being about 910. Either of n or n' may individually be 420 or 520, or both may be 420 or 520, or both may be 455. The preferred ratio of n to n' is from about 0.5 to 1.5, with an especially preferred ratio of from about 0.8 to about 1.2. A molecular weight of "about" a certain number means that it is within a reasonable range of that number as determined by conventional analytical techniques.

Also preferred is a conjugate of Formula I where IFNα is IFNα2a, a conjugate where R and R' are methyl, a conjugate where X is NH, and a conjugate where n and n' are individually or both either 420 or 520. Such a conjugate having all the above characteristics is especially preferred.

R and R' may be any lower alkyl, by which is meant an alkyl group having from one to six carbon atoms such as methyl, ethyl, isopropyl, etc. Branched alkyls are included. A preferred alkyl is methyl. With regard to the two PEG groups of Formula I, R and R' may be the same or different.

By IFNα (interferon α) and its species IFNα 2a is meant the natural or recombinant protein, preferably human, as obtained from any conventional source such as tissues, protein synthesis, cell culture with natural or recombinant cells. Any protein having the activity of IFNα, such as muteins or otherwise modified proteins, is encompassed. Obtaining and isolating IFNα from natural or recombinant sources is well known (Pestka I) A preferred IFNα is IFNa α2a, which as stated above is obtained by known methods (Pestka II).

The physiologically active conjugate of Formula I has IFNα activity, by which is meant any fraction or multiple of any known IFNα activity, as determined by various assays known in the art. In particular, the conjugate of this invention has IFNα activity as shown by antiproliferative activity against tumor cells and antiviral activity against cells infected with a virus. These are known activities of IFNα. Such activity in a conjugate can be determined by assays well known in the art, for example the assays described below (see also Rubinstein, Borden).

The conjugate of Formula I is produced by covalent linkage of IFNα to PEG which has been activated by replacement of the PEG hydroxyl with a linking group, forming a reagent which is an N-hydroxy succinimide ester derivative of PEG (in particular monomethoxy PEG) of Formula II. The reagent may be obtained by conventional methods (Monfardini). Linkage is via an amide or ester bond. In a preferred conjugate, linkage is via an amide bond (X is NH).

X represents the attachment site on IFNα by which the PEG reagent of Formula II is covalently attached to the IFNα. The reagents attach to primary amino groups (XH ⊂ NH₂) on for example lysine or to the N-terminus of the IFNα. The reagents can also attach to a hydroxy (XH=OH) on for example serine.

The reagent of formula II (PEG2-NHS), in which a total of 2 monomethoxy PEG (m-PEG) chains linked to lysine, one each at the α and ε amino groups via carbamate (urethane) bonds and having the lysine carboxyl group activated to a succinimidyl ester, may be obtained by conventional methods, according to known procedures (Monfardini) applicable to a reagent with R is lower alkyl, and a desired n. The reagent may be obtained from Shearwater Polymers, Inc. (Huntsville, Ala.). The preferred average MW of the PEG obtained is about 20,000 daltons, providing a total PEG mass of about 40,000 daltons in PEG2-NHS (other MWs may be obtained by varying n for the PEG-alcohol starting materials for the reagent of Formula II, by conventional methods).

The reagent of formula II may be conjugated to IFNα by conventional methods. Specifically, the reagent of Formula II primarily reacts with one or more of the primary amino groups (for example N-terminus and lysine side chains) of IFNα (for example IFN α-2a) to form an amide linkage between the IFNα and the polymer backbone of PEG. The PEGylation reaction can also take place between PEG2-NHS and the free (if any) hydroxyl groups (for example serine) of IFNα to form an ester linkage. The reaction mechanism is shown above. The reaction conditions are conventional to a skilled person, and are provided in detail below. The PEG reagent is combined with IFNα under mildly basic conditions at low temperature under conditions suitable for a nucleophilic substitution which will produce the conjugate of Formula I. This is also shown in the above reaction mechanism.

Attaching the reagents to IFNα may be accomplished by conventional methods. PEGs of any selected MW of this invention may be used (n). Reaction conditions may be selected to provide the claimed conjugate with one reagent attached. The conjugate of Formula I, which has a single reagent of Formula II attached, is separated from unmodified IFNα and conjugates having attached more than one reagent molecule by conventional methods. Purification methods such as cation exchange chromatography may be used to separate conjugates by charge difference, which effectively separates conjugates into their various molecular weights. The content of the fractions obtained by cation exchange chromatography may be identified by molecular weight using conventional methods, for example, mass spectroscopy, SDS-PAGE, or other known methods for separating molecular entities by molecular weight. A fraction then is accordingly identified which contains the conjugate of Formula I purified free from unmodified IFNα and from conjugates having more than one reagent attached. In addition, the reagents of Formula II release one lysine per reagent upon acid hydrolysis, so that the number of lysines in the hydrolysis indicates the number of PEGs attached to the protein, thus the number of reagent molecules attached to a conjugate may be verified.

The following Examples are provided to illustrate the invention and do not limit it in any way. IFNα2a is used in these examples. Other species of IFNα may also be conjugated to PEG by the methods exemplified.

Materials and Methods

Materials

Interferon α-2a was prepared by known methods (Pestka II). Polyethylene glycol (PEG) reagent of formula II was purchased from Shearwater Polymers, Inc. (Huntsville, Ala.). Fractogel® EMD CM 650(S) resin, with particle sizes 25–40 μm, were supplied by EM Separations (Gibbstown, Mass.). Concentrated (10×) phosphate buffered saline (PBS), pH 7.3, was purchased from BioWhittaker (Walkersville, Md.). Sodium dodecyl (laurel) sulfate/polyacrylamide gel electrophoresis (SDS-PAGE) pre-cast gels and electrophoresis units were obtained from NOVEX (San Diego, Calif.). Concentrated Fast Stain for protein staining of PEG conjugates on SDS-PAGE was purchased from Zoion Research, Inc. (Newton, Mass.). The LAL endotoxin assay kit was purchased from Associates of Cape Cod, Inc. (Woods Hole, Mass.). All other reagents used were of the highest quality available. The jugular cannulated rats and BDF-1 mice were supplied by Charles River Laboratories (Wilmington, Mass.).

1. Experimental Procedures 1.1. Small Scale Preparation of Conjugate of Formula I Two hundred-eight milligrams (5.2 μmol) of the reagent of Formula II (average MW of 40,000 daltons) was added to 50 mg (2.6 μmol) of IFNα in 10 ml of 100 mM borate, pH 8.0. Final protein: reagent molar ratio was 1:2. The reaction mixture was stirred at 4° C. for 2 hours. The reaction was stopped by adjusting the pH to 4.5 with glacial acetic acid.

The reaction mixture was diluted 50-fold with water, filtered through a 0.2μ filter and applied onto an Amicon column packed with 100 ml (3.2×13 cm) Fractogel EMD CM 650(S), at a flow rate of 20 ml/min. The column was previously equilibrated with 10 mM ammonium acetate, pH 4.5. The column effluent was monitored by UV absorbance at 280 nm. The column was then washed with the equilibration buffer until UV absorbance returned to baseline. PEG-IFN conjugates having more than one reagent of Formula II attached (PEG-IFN oligomers) were eluted with 40 mM ammonium acetate, pH 4.5 and the conjugate of Formula I was eluted with 0.12M NaCl in the 40 mM ammonium acetate buffer. The unmodified IFN remaining in the column was eluted with 0.5M NaCl in the same buffer. The column was regenerated by a 1.0M NaCl wash followed by the equilibration buffer wash. The pooled fractions of the conjugate of Formula I were concentrated in an Amicon stirred cell concentrator fitted with a YM10 membrane to approximately 1 mg/ml concentration.

The Fractogel CM 650(S) cation exchange resin used for purification, adsorbed the PEG and unmodified IFN effectively. The strength of adsorption was dependent upon the degree of PEGylation. The conjugates bound less tightly than the unmodified IFN. The PEG-IFN oligomers were eluted with 40 mM ammonium acetate, while the conjugate of Formula I eluted with 0.12M NaCl. The unmodified IFN eluted with 0.5M NaCl. All preparations contained <5 EU/mg endotoxins. The resulting preparation contained >99% of conjugate of Formula I and was free of unmodified IFN.

1.2. Large-Scale Preparation of Conjugate of Formula I

Six thousand two hundred and forty milligrams (156 μmol) of the reagent of Formula II (average molecular weight of 40,000 daltons) was dissolved in 63 ml of 1 mM HCl at 4 degrees C. and quickly added to 125 ml of a solution containing 1000 mg (52 μmol) of interferon in 50 mM borate buffer pH 9.0. The final protein:reagent ratio was 1:3 and the final reaction mixture protein concentration was 5.3 mg/ml. The reaction mixture was stirred for 2 hours at 4 degrees C. The reaction was stopped by adjusting the pH to 4.5 with glacial acetic acid.

The reaction mixture was diluted 10-fold with water and applied onto a column packed with 600 ml Fractogel EMD CM 650(M) previously equilibrated with 20 mM sodium acetate, pH, 4.5 at a linear velocity of 1.3 cm/min. The column was washed with the equilibration buffer followed by 10 mM NaCl to remove excess reagent, reaction byproducts and PEG-IFN oligomers. The conjugate of Formula I was eluted with the equilibration buffer containing 200 mM NaCl. The unmodified interferon still adsorbed to the column was removed by washing with 750 mM NaCl in the equilibration buffer. The conjugate of Formula I, which was eluted at 0.3–0.5 mg/ml was further concentrated and diafiltered into the final formulation buffer, 20 mM sodium acetate, pH, 5.0 containing 150 mM NaCl. The overall yield of the conjugate of Formula I was 40 . 45%.

The purified PEG-IFN from the large-scale preparation consists of >99% conjugate of Formula I. The average molecular weight of the conjugate of Formula I of this example is 62,000 daltons, including the molecular weight of IFNα-2a which is 19,241 daltons, and the average molecular weight of the reagent which is between 40,000 and 45,000 daltons, about 43,000 daltons.

Characterization 2.1. Protein Determination

Protein concentrations were determined using an $A_{280}$ value of 1.0 for a 1 mg/ml solution of IFNa α-2a.

2.2. SDS-PAGE Analysis

The conjugate was analyzed by sodium dodecyl (lauryl) sulfate/polyacrylamide (8–16%) gel electrophoresis, under reducing conditions, according to the methods of Laemmli. SDS-PAGE containing PEG-conjugates were stained for protein using Fast Stain, according to the manufacturer's instructions.

2.3. Determination of Endotoxin Levels

Endotoxin levels were determined using the LAL method, according to the manufacturer's instructions. All preparations contained <5 EU/mg endotoxins.

3. In Vitro Bioactivities of Conjugate of Formula I as Prepared in Example 1.1

3.1. Antiviral Activity in Bovine Kidney Cells

The in vitro antiviral activity of IFNa α-2a and the conjugate of Formula I were determined in a cell culture bioassay employing Madin-Darby bovine kidney cells challenged with vesicular stomatitis virus (Rubinstein). The antiviral activities are listed in Table 1, along with their corresponding residual activities as a percentage of the starting IFN.

TABLE 1

Anti-Viral Activities

| Samples | PEG Type | Total PEG Mass (kDa) | # Lys Modified | Specific Activity (U/mg) | Residual Activity (%) |
|---|---|---|---|---|---|
| IFN | NA | NA | NA | $2.00 \times 10^8$ | 100 |
| Conjugate of Formula I | Branched | 40 | 1 | $1.40 \times 10^7$ | 7 |

4. Pharmacokinetics

Female Sprague Dawley rats, surgically implanted with jugular cannulas, with an average body weight of 240–260 g were housed individually, allowed free access to food and water and maintained in a 12 hour light-dark cycle. Within 4–6 hours after arrival, jugular cannulas were flushed with PBS. The following day, after flushing with 0.15–0.2 ml PBS, $2 \times 10^6$ units of IFNα in 0.2–0.4 ml PBS was injected, followed by injection of 0.15–0.2 ml PBS to assure that all drug was washed into the animal. Thus each animal received a dosage of $8 \times 10^6$ IFNα units/kg body weight.

Blood samples were drawn at 5, 15 and 30 minutes, as well as, 1, 3, 5, 12 and 24 hours after injection of IFN and the conjugate. At all time points, after discarding the first 0.15–0.2 ml of blood, an aliquot of 0.5 ml blood was withdrawn using a fresh syringe via the jugular cannula. The samples were discharged into serum separating tubes at room temperature. Once all the samples were collected for the time points, the tubes were centrifuged at 14,000×g in a refrigerated Eppendorf centrifuge for 10 minutes. The separated serum was transferred into 1.5 ml microfuge tubes and frozen at −80° C., until ready for bioassay. Serum samples were diluted appropriately and the antiviral activity at each time-point was determined as described. From the plot of time vs. activity, the terminal half-life of the conjugate of Formula I and IFNα were determined and listed in Table 3, which also include plasma residence times.

TABLE 3

Terminal Half-Lives and Mean Plasma Residence Time

| Sample | $t_{1/2}$ (hours) | Plasma Residence Time (hours) |
|---|---|---|
| IFN | 2.1 | 1.0 |
| Conjugate of Formula I | 15.0 | 20.0 |

Terminal $t_{1/2}$ estimated by log linear regression.

Immunogenicity

Normal BDF-1 mice (ten per group) were injected intraperitonially once per day five times per week with various interferon preparations having 300,000 units of antiviral activity. Some mice were also injected with aggregated form of IFN-2a which is more immunogenic than the monomer form. Blood samples were taken 19 days following the last injection and the serum was evaluated for neutralizing antibodies.

As seen in Table 4, mice injected with IFNα-2a produced neutralizing antibodies and this response was greatly increased in mice injected with interferon aggregates. No antibodies were detectable in the majority of animals injected with the conjugate of this invention.

TABLE 4

Immunogenicity

| | Antibody (INU/ml)* | |
|---|---|---|
| Treatment | Median | Range |
| IFN α2a | 2,400 | 217–8,533 |
| IFN α2a Aggregates | 42,667 | 8,000–768,000 |
| Conjugate of Formula I | 0 | 0–1,133 |

*Interferon neutralizing units/ml

Antitumor Activity In vivo

The in vivo antitumor activity of a conjugate of Formula I (PEG2-IFN alpha-2a) and unmodified IFN alpha-2a were evaluated by determining their ability to reduce the size of various human tumor cells implanted subcutaneously into mice. Results are shown in FIGS. 1–6.

Procedure: Athymic nude mice (Harlan) received a subcutaneous implant under the left rear flank of $2 \times 10^6$ human renal A498 cells (FIGS. 1 and 2), human renal ACHN cells (FIGS. 3 and 4), or human renal G402 cells (FIGS. 5 and 6). 3 to 6 weeks were allowed for the tumors to become established, as indicated. The size criteria for acceptance into the study was 0.05 to 0.50 cubic centimers (vol=L×W²). The mice were given total weekly doses of PEG2-IFN alpha-2a or unmodified IFN alpha-2a of 30, 60, 120 or 300 μg. In the case of PEG2-IFN alpha-2a the mice were treated one time per week (Monday) with 30, 60, 120 or 300 μg of PEG2-IFN alpha-2a per treatment. In the case of unmodified IFN alpha-2a the mice were treated three times per week (Monday, Wednesday, Friday) with 10, 20, 40 or 100 μg of IFN alpha-2a per treatment. The duration of treatment was 4 to 5 weeks depending on tumor agressiveness. Tumor volumes were measured every Monday prior to treatments.

Figure 1:
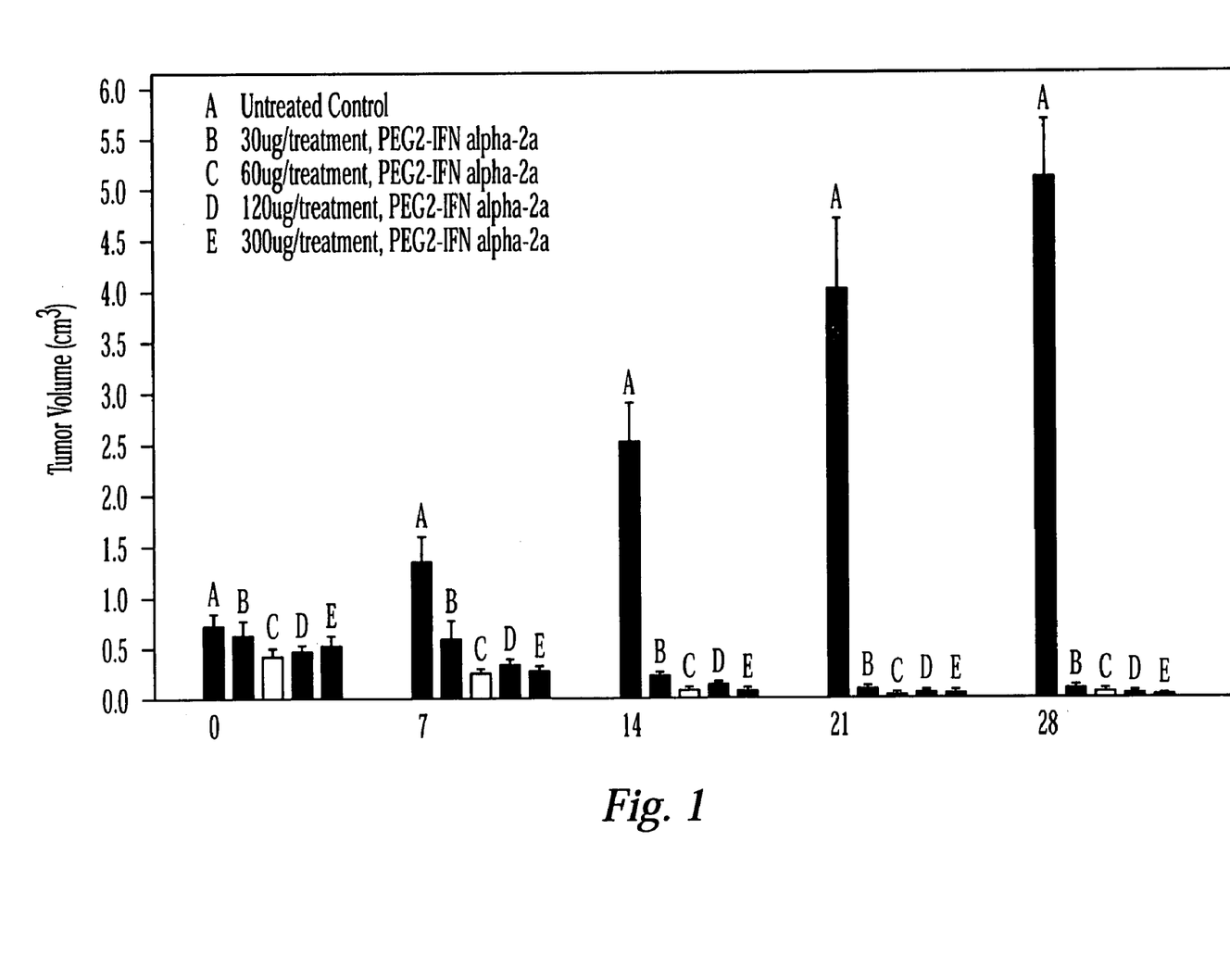
FIG. 1: Antitumor activity of the PEG2-IFN alpha-2a in nude mice implanted subcutaneously with human renal A498 cells.
Figure 2:
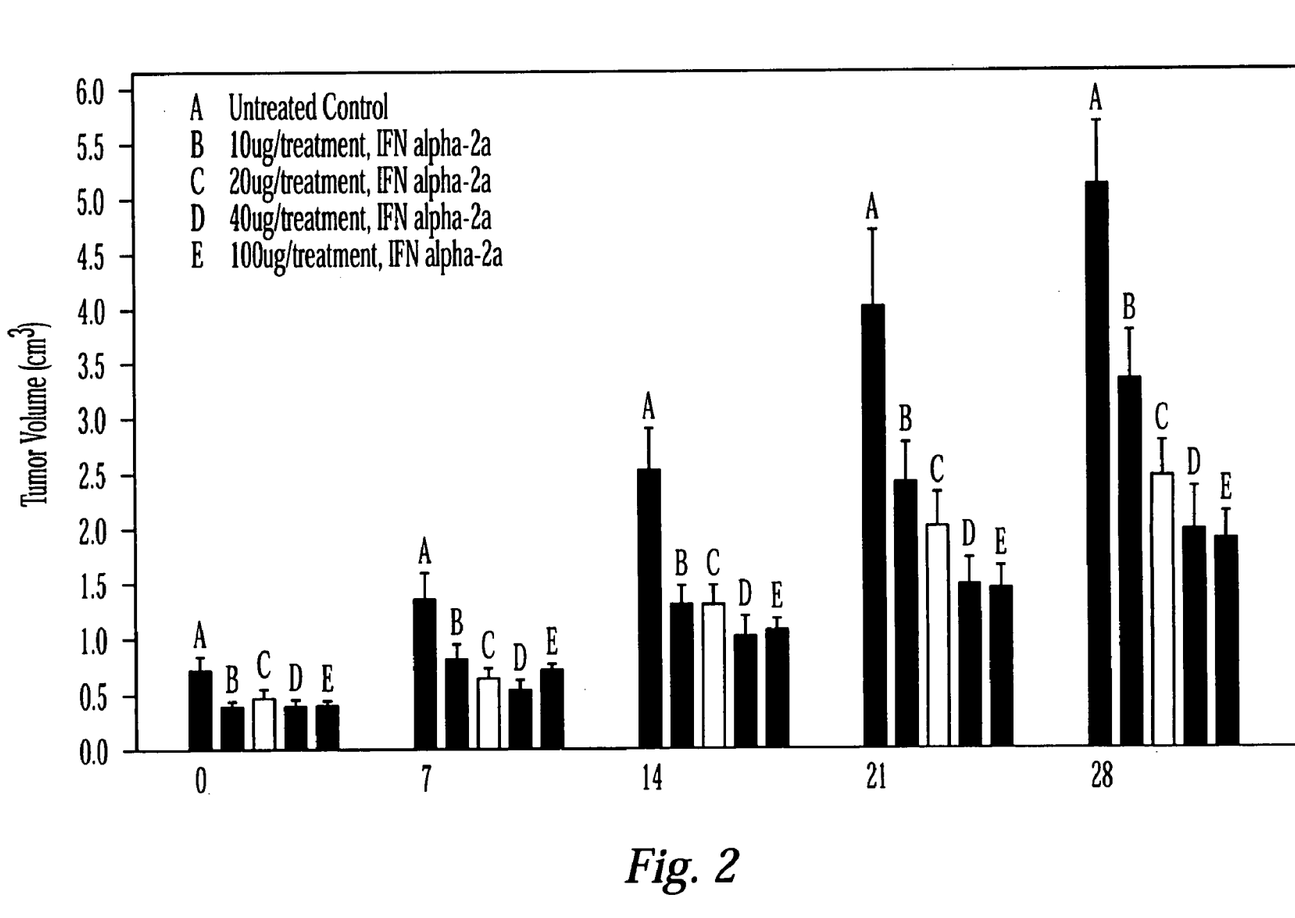
FIG. 2: Antitumor activity of IFN alpha-2a in nude mice implanted subcutaneously with human renal A498 cells.

Results: PEG2-IFN alpha-2a showed a marked reduction in A498 tumor size as compared to unmodified IFN alpha-2a for all weekly dosage levels tested, at 7 days, 14 days, 21 days and 28 days after the beginning of treatment (FIGS. 1 and 2). Treatment continued for four weeks. Seven days after treatment was discontinued three mice in each group were sacrified. In the three mice treated with PEG2-IFN alpha-2a no residual tumor was observed. In mice treated with unmodified IFN alpha-2a the A498 tumor weight was 1.28 grams, 0.62 grams, and 1.60 grams respectively in each of three mice. The A498 tumor weight was 2.32 grans, 2.37 grams, and 1.94 grams in each of three control mice. At 80 days after the end of the four week treatment period the existence of tumors was determined by palpation in seven mice. All seven mice were free of tumor tissue by palpation.

Figure 3:
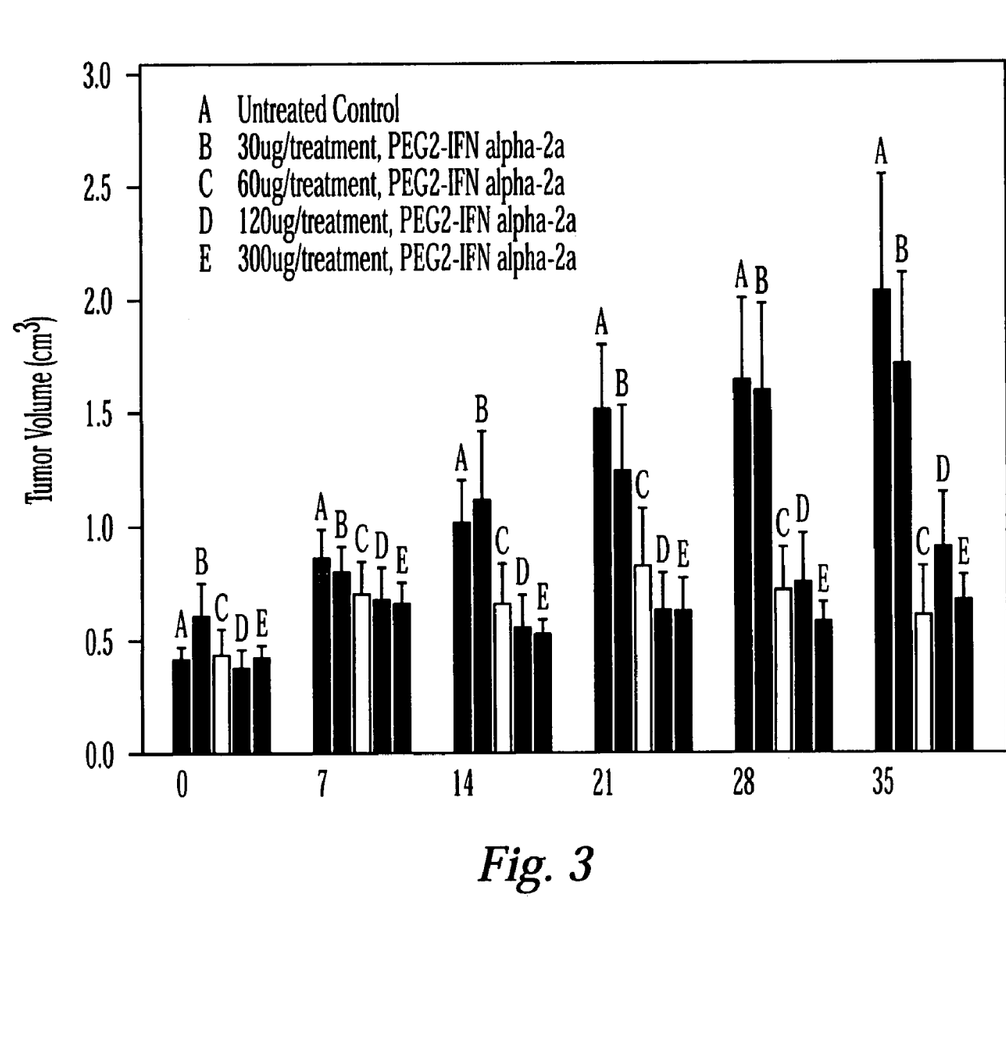
FIG. 3: Antitumor activity of PEG2-IFN alpha-2a in nude mice implanted subcutaneously with human renal ACHN cells.
Figure 4:
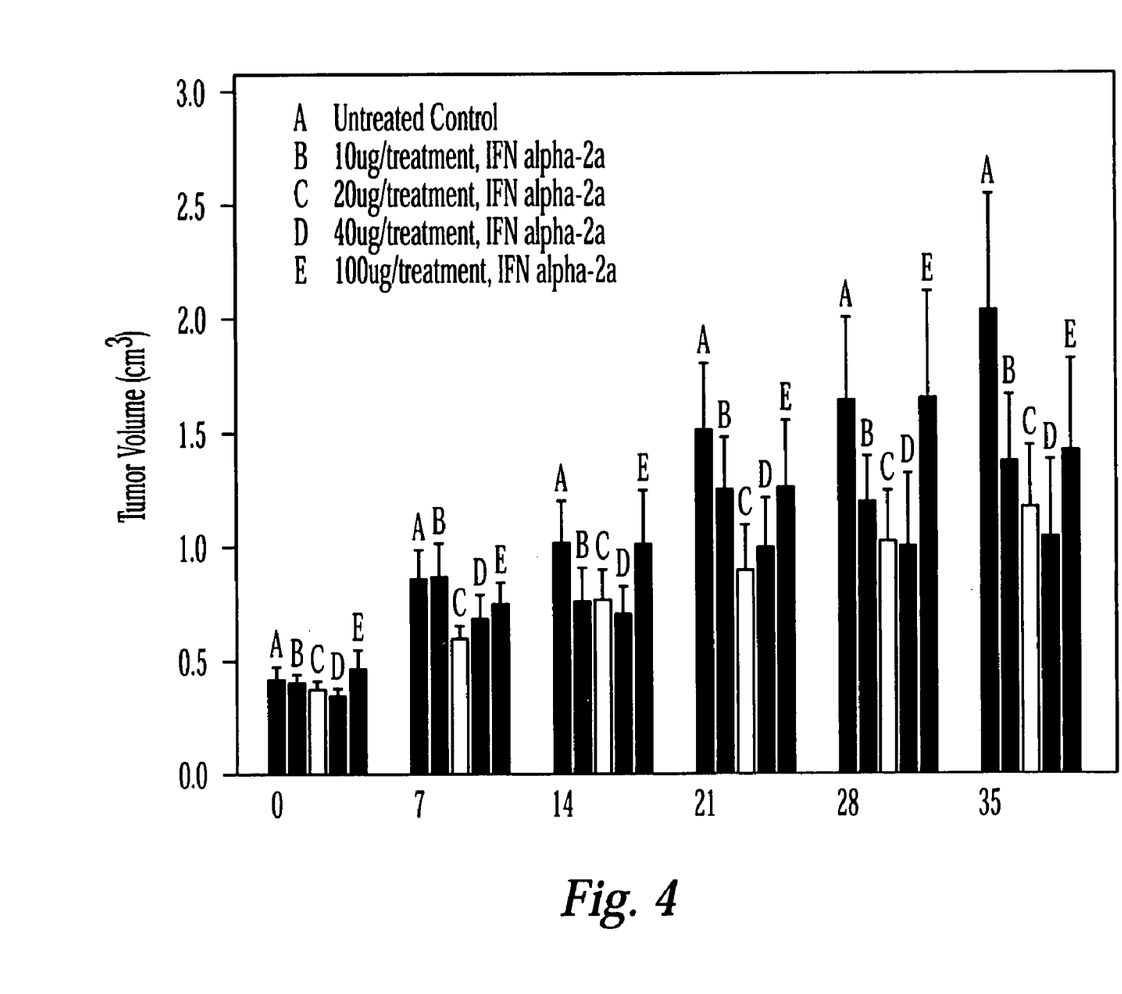
FIG. 4: Antitumor activity of IFN alpha-2a in nude mice implanted subcutaneously with human renal ACHN cells.

PEG-IFN alpha-2a showed a significant reduction in ACHN tumor size as compared to unmodified IFN alpha-2a for weekly dosage levels of 60, 120, and 300 μg, at 14 days, 21 days, 28 days and 35 days (FIGS. 3 and 4).

Figure 5:
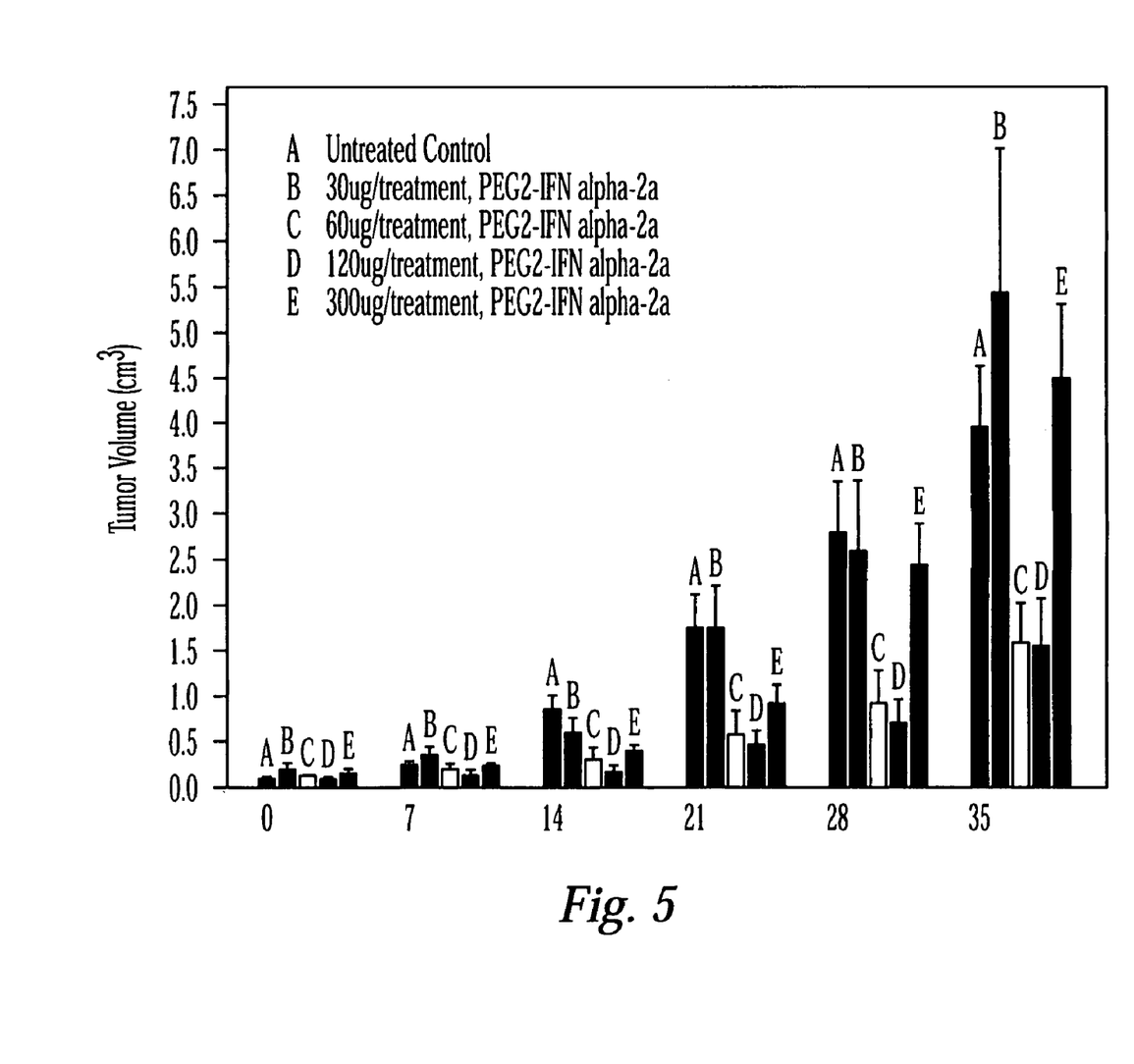
- FIG. 5: Antitumor activity of PEG2-IFN alpha-2a in nude mice implanted subcutaneously with human renal G402 cells.
Figure 6:
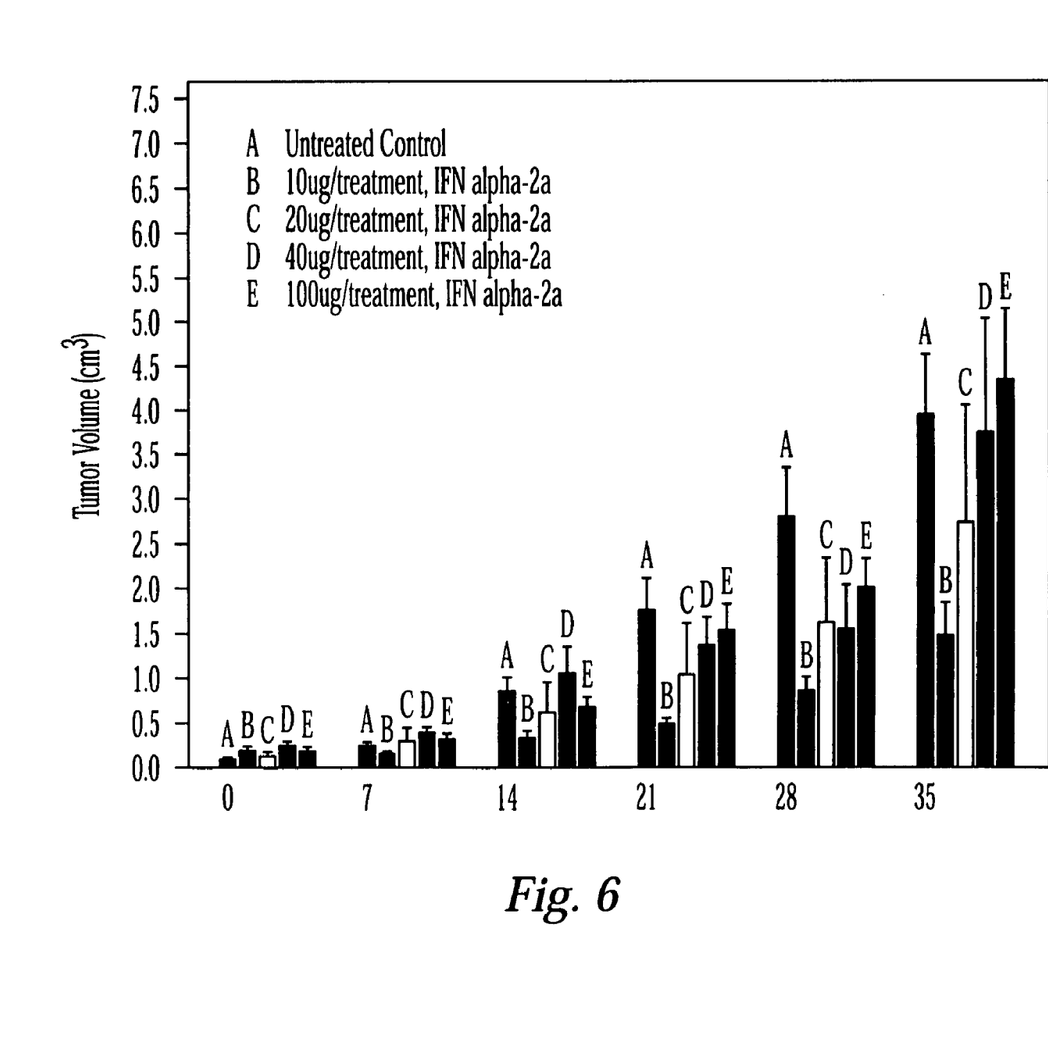
FIG. 6: Antitumor activity of IFN alpha-2a in nude mice implanted subcutaneously with human renal G402 cells.

PEG2-IFN alpha-2a showed a significant reduction in G402 tumor size as compared to unmodified IFN alpha-2a for weekly dosage levels of 60 and 120 μg, at 14 days, 21 days, 28 days and 35 days (FIGS. 5 and 6).

REFERENCES

1. Y. Inada, A. Matsshima, Y. Kodera and H. Nishimura, Polyethylene glycol(PEG)-protein conjugates: Application to biomedical and biotechnological processes, J. Bioact. and Compatible Polymers, 5:343 (1990)
2. C. Delgado, G. E. Francis and D. Fisher, The uses and properties of PEG-linked proteins, Critical Reviews in Therapeutic Drug Carrier Systems, 9:249 (1992)
3. N. V. Katre (I), The conjugation of proteins with PEG and other polymers; altering properties to enhance their therapeutic potential, Advanced Drug Delivery Systems, 10:91 (1993)
4. N. V. Katre (II), M. J. Knauf and W. J. Laird, Chemical modification of interleukin-2 by PEG increases its potency in the murine Meth A sarcoma model, Proc. Natl. Acad. Sci. USA, 84:1487 (1987)
5. R. Satake-Ishikawa, M. Ishikawa, Y. Okada, M. Kakitani, M. Kawagishi, S. Matsuki and K. Asano, Chemical modification of recombinant granulocyte colony stimulating factor by PEG increases its biological activity in vivo, Cell Structure and Function, 17:157–160 (1992)
6. H. Hiratani, Long-acting Composition, U.S. Pat. No. 4,609,546 (1986)
7. C. S. Monfardini, O. Schiavon, P. Caliceti, M. Morpurgo, J. M. Harris and F. M. Veronese, A branched monomethoxypoly(ethylene glycol) for protein modification, Bioconjugate Chem. 6:62 (1995)
8. Y. Tsutsumi, T. Khira, S. Yamamoto, M. Kubo, S. Nakagawa, M. Miyake, Y. Horisawa, T. Kanamori, H. Ikegami and T. Mayumi, Chemical modification of natural tumor necrosis factor-α with polyethylene glycol increases its potency, Jpn. J. Cancer Res. 85:9 (1994).
9. H. Inoue, T. Kadoya, K. Kabaya, K. Tachibana, N. Nishi, M. Sato, M. Oshasava, T. Mikayama and K. Mori, A highly enhanced thromobopoietic activity by polyethylene glycol-modified recombinant IL-6, J. Lab. Clin. Med. 124:529 (1994).
10. S. M. Chamow, T. P. Kogan, M. Venuti, T. Gadek, R. J. Harris, D. H. Peers, J. Mordenti, S. Shak and A. Ashkenazi, Modification of CD4 immunoadhesion with monomethoxypoly(ethylene glycol) aldehyde via reductive alkylation Bioconj. Chem. 5:133, 1994
11. S. Pestka (I) The human interferons from protein purification and sequence to cloning and expression in bacteria: before, between, and beyond. Arch. Biochem. Biocphys. 221:1 (1983)

12. S. Pestka (II), The purification and manufacture of human interferons. Sci. Am. 249:36 (1983)
13. S. Rubinstein, P. C. Familletti and S. Pestka, Convenient assay for IFNas, J. Virol. 37:755 (1981)
14. E. C. Borden, T. F. Hogan, and J. G. Voelkel, Comparative antiproliferative activity in vitro natural interferons α and β for diploid and transformed human cells, Canc. Res. 42:4948 (1982)
15. U. K. Laemmli, Cleavage of structural protein during assembly of the head bacteriphage T4. Nature 227:680 (1970)

What is claimed is:

1. A PEG-IFNα2a conjugate having the formula

I wherein R and R' are each methyl; X is NH; n and m are integers having a sum such that the total polyethylene glycol mass of said conjugate is about 40,000 daltons.

2. The conjugate of claim 1 wherein the average sum of n and m is about 910.

3. The conjugate of claim 1 wherein one of n and m is 420.

4. The conjugate of claim 1 wherein one of n and m is 520.

5. The conjugate of claim 1 wherein each of n and m is independently 455.

6. A method of inhibiting the proliferation of a cancer cell comprising contacting the cancer cell with the PEG-IFNα2a conjugate of claim 1.

7. A method of treating a proliferative disorder in an animal comprising the step of administering to the animal a therapeutically effective amount of the PEG-IFNα2a conjugate of claim 1.

8. The method of claim 7 wherein the animal is a human.

9. The method of claim 7 wherein the proliferative disorder is selected from the group consisting of hairy cell leukemia, chronic myelogenous leukemia and Kaposi's sarcoma.

10. The method of claim 7 wherein the proliferative disorder is a renal proliferative disorder.

11. A method of inhibiting the growth or replication of a virus in a plurality of cells comprising the step of contacting one of the cells with the PEG-IFNα2a conjugate of claim 1.

12. A method of treating a viral infection in an animal comprising the step of administering to the animal a therapeutically effective amount of the PEG-IFNα2a conjugate of claim 1.

13. The method of claim 12 wherein the animal is a human.

14. A composition comprising the conjugate of claim 1 in an aqueous solution.

15. The composition of claim 14 wherein the PEG-IFNα2a conjugate is separated by cation exchange chromatography from unmodified IFNα2a and from PEG-IFNα2a conjugates having more than one branched polyethylene glycol attached.

16. The composition of claim 14 wherein the composition is free from unmodified IFNα2a and from PEG-IFNα2a conjugates having more than one branched polyethylene glycol attached.

17. The composition of claim 14 that is at least about 99% by weight, relative to the amount of the PEG-IFNα2a conjugate, free from unmodified IFNα2a and from PEG-IFNα2a conjugates having more than one branched polyethylene glycol attached.

18. The composition of claim 14 that has about 7% of the antiviral Residual Activity of a composition of a similar amount of unmodified IFNα-2a when determined in a cell culture bioassay employing Madin-Darby kidney cells challenged with vesicular stomatitis virus.

* * * * *